(12) United States Patent
van Liesdonk et al.

(10) Patent No.: US 11,914,738 B2
(45) Date of Patent: Feb. 27, 2024

(54) CATEGORIZING A SENSITIVE DATA FIELD IN A DATASET

(71) Applicant: KONINKLIJKE PHILIPS N.V., Eindhoven (NL)

(72) Inventors: Peter Petrus van Liesdonk, Eindhoven (NL); Daniel Pletea, Eindhoven (NL); Paul Koster, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 127 days.

(21) Appl. No.: 17/267,838

(22) PCT Filed: May 14, 2020

(86) PCT No.: PCT/EP2020/063561
§ 371 (c)(1),
(2) Date: Feb. 11, 2021

(87) PCT Pub. No.: WO2020/229644
PCT Pub. Date: Nov. 19, 2020

(65) Prior Publication Data
US 2021/0248263 A1 Aug. 12, 2021

Related U.S. Application Data

(60) Provisional application No. 62/848,180, filed on May 15, 2019.

(51) Int. Cl.
*G06F 21/62* (2013.01)
*G16H 70/60* (2018.01)
(Continued)

(52) U.S. Cl.
CPC ........ *G06F 21/6227* (2013.01); *G06F 21/602* (2013.01); *G16H 70/60* (2018.01); *H04L 9/008* (2013.01); *H04L 2209/42* (2013.01)

(58) Field of Classification Search
CPC ... G06F 21/6227; G06F 21/602; G16H 70/60; H04L 9/008; H04L 2209/42; H04L 2209/88
See application file for complete search history.

(56) References Cited

U.S. PATENT DOCUMENTS 9,361,480 B2   6/2016   Kolesnikov
2012/0072992 A1*  3/2012   Arasaratnam ....... G06F 21/6227
                                                              726/26
(Continued)

FOREIGN PATENT DOCUMENTS

WO    2017171726 A1   10/2017

OTHER PUBLICATIONS

Elixhauser, A. et al., "Comorbidity measures for use with administrative data". Med Care., 36(1):8-27, 1998.
(Continued)

*Primary Examiner* — Meng Li

(57) ABSTRACT

Some embodiments are directed to a categorization system for categorizing a sensitive data field in a dataset, e.g., a disease classification according to the ICD classification. A client device is to obtain categories for one or more records of the dataset. The client device determines categorization data for the categorization. The categorization data comprises homomorphic encryptions of possible values of the sensitive data field and encodings of the categories associated to the respective possible values, thus keeping the categorization secret. A data provider device stores the dataset and determines homomorphic encryption indicating differences between the value of the sensitive data field for a record and respective possible values. A categorization device determines which of those encryptions indicates a match and provides a category encoding associated with a (Continued)

matching possible value to the client device. The client device associates the encoded category to the record.

13 Claims, 8 Drawing Sheets

(51) Int. Cl.
 *G06F 21/60* (2013.01)
 *H04L 9/00* (2022.01)

(56) References Cited

U.S. PATENT DOCUMENTS

| | | | | |
|---|---|---|---|---|
| 2013/0291060 | A1* | 10/2013 | Moore | G06F 16/83 |
| | | | | 726/1 |
| 2015/0278549 | A1* | 10/2015 | Kolesnikov | H04L 65/60 |
| | | | | 713/193 |
| 2016/0119119 | A1 | 4/2016 | Calapodescu | |
| 2017/0124335 | A1* | 5/2017 | Freudiger | G06F 21/6254 |
| 2017/0337397 | A1* | 11/2017 | Tang | H04L 63/20 |
| 2019/0281066 | A1* | 9/2019 | Simons | G06F 21/6254 |
| 2019/0370334 | A1* | 12/2019 | Bhowmick | G06F 40/242 |
| 2020/0327252 | A1* | 10/2020 | McFall | G06F 21/78 |
| 2021/0248263 | A1* | 8/2021 | van Liesdonk | H04L 9/008 |

OTHER PUBLICATIONS

Kantarcioglu, M. et al., "Formal anonymity models for efficient privacy-preserving joins", Data & Knowledge Engineering, vol. 68, No. 11 (Nov. 1, 2009), pp. 1206-1223.

Pletea, D. et al., "Invention Disclosure: Privacy Preserving Data Categorization". Jun. 1, 2018, http://www.who.int/classifications/icd/en/.

* cited by examiner

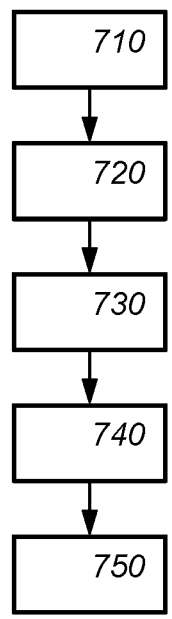 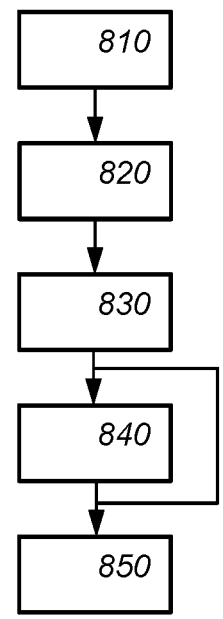
Fig. 7a   Fig. 7b
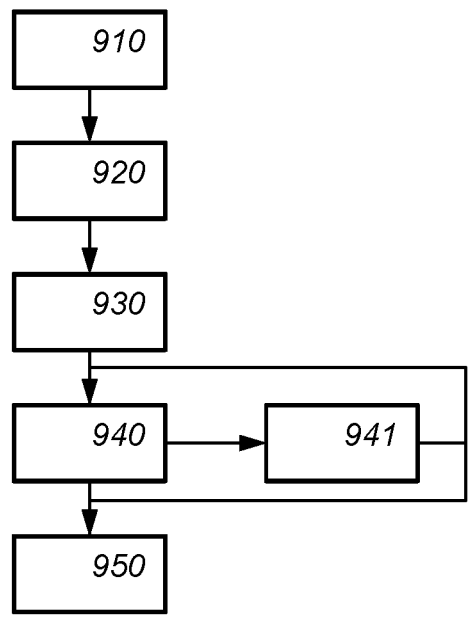
Fig. 7c

CATEGORIZING A SENSITIVE DATA FIELD IN A DATASET

CROSS-REFERENCE TO PRIOR APPLICATIONS

This application is the U.S. National Phase application under 35 U.S.C. § 371 of International Application No. PCT/EP2020/063561, filed on May 14, 2020, which claims the benefit of U.S. Patent Application No. 62/848,180, filed on May 15, 2019. These applications are hereby incorporated by reference herein.

FIELD OF THE INVENTION

The invention relates to a categorization system, a client device, a data provider device, and a categorization device. The invention further relates to methods corresponding to the respective devices, and to a computer readable storage medium.

BACKGROUND

In medical research, researchers typically use multiple datasets, for instance, for training and validation of machine learning algorithms and models, or for medical hypothesis testing. Having access to more and better-quality data typically results in better-quality results. Therefore, researchers often request data from other institutions for analysis. However, gaining such access can be challenging due to the fact that the requested data is typically privacy-sensitive, e.g., containing detailed disease classifications according to the ICD, International Classification of Diseases, classification, or location information like ZIP codes. Exchange of such privacy-sensitive information is often restricted by various privacy regulations, such as the HIPPA, Health Insurance Portability and Accountability Act, in the United States and the GDPR, General Data Protection Regulation, in the European Union.

Given such sensitive data, the data provider often cannot directly share it. Various measures can be taken to still allow some use of the data, e.g., removal of sensitive data points that make some patients outliers, or insertion of noise. In particular, one useful technique for the data provider to reduce privacy-sensitivity of sensitive data fields is to categorize the sensitive data field before providing the dataset to the researcher, e.g., to group sensitive values together depending on the research purpose of the recipient. This way, it is possible to still make use of the sensitive data field without the need to disclose exact values. For example, in "Comorbidity measures for use with administrative data" by A. Elixhauser et al., Med Care., 36(1):8-27, 1998, it is disclosed to categorize co-morbidities of patients based on the ICD classification by means of the so-called Elixhauser Comorbidity Index method.

SUMMARY OF THE INVENTION

As the inventors realized, the existing technique of letting the data provider perform a categorization of a dataset before providing it to a client, has several shortcomings. One concern is that the categorization method to be used is, in many cases, not open to the public. For example, a medical researcher may not want to disclose to other institutions details about a hypothesis being tested or a type of data used to train a machine learning model. Moreover, the categorization may contain sensitive intellectual property that a researcher or other party obtaining a dataset has a legitimate interest in protecting. Hence, in various situations it can be undesirable for data providers or other external parties to learn the categorization to be performed.

To better address these and other concerns when categorizing data, a categorization system is proposed as defined by the claims, as well as a client device, a data provider device, and a categorization device for use in such a categorization system. The categorization system may be for categorizing a sensitive data field in a dataset. The dataset may comprise one or more records. Each record of the dataset may comprise a value of the sensitive data field.

The client device may be for obtaining the categorization. The data provider device may store the dataset and may be for providing data to be categorized. Interestingly, to enable the categorization, a categorization device may be used, but in such a way that the categorization device may not learn either the dataset or the categorization. That is, no fully trusted categorization device may be needed.

To perform the categorization, the client device may determine categorization data and provide it to the data provider device. The categorization data may comprise, for one or more possible values of the sensitive data field, a homomorphic encryption of the possible value and data encoding a category of the possible value. As is known in the art, a homomorphic encryption is a type of encryption that allows to perform certain operations in the encrypted domain, e.g., without performing decryption or even knowing the decryption key. For example, in various embodiments, additively homomorphic encryption is used in which, given two encrypted values, an encryption of the sum of the two values can be determined without decrypting or even being able to decrypt the encryptions. Similarly, given an encrypted value and a factor, an encryption of the product of the factor and the encrypted value can be determined without decryption. The decryption key of the homomorphic encryption may be known by the categorization device but not by the data provider device.

Having obtained categorization data comprising such a homomorphic encryption of a possible value, the data provider device may determine, for a record of the dataset, a homomorphic encryption indicative of a difference between the possible value and a value of the sensitive data field for the record, based on the homomorphic encryption of the possible value. For example, the encryption can be zero if the possible value is equal to the value for the record and non-zero otherwise. Interestingly, because the encryption is a homomorphic encryption, the data provider device can determine this difference encryption without needing to perform decryption, and in particular, without knowing the possible value or whether it matches the value for the record. The data provider may provide the difference encryption along with data encoding the category of the possible value to the categorization device.

Having obtained such a difference encryption with respect to a record and a possible value, and such a category encoding, the categorization device may determine if the value of the sensitive data field for the record matches the possible value based on the difference encryption. The categorization device may be able to do this because it knows the decryption key for the homomorphic encryption, e.g., by decrypting the difference encryption and checking whether it equals zero. Interestingly, however, the categorization device learns may learn neither the value of the sensitive data field for the record nor the possible value, e.g., because the decrypted value just indicates whether they are equal. Moreover, the categorization device may not learn the category because it is encoded. Nonetheless, the categorization device may be able to determine whether there is a match and, in that case, associate the encoded category to the record.

The categorization device may further provide, to the client device, data encoding the category associated to the record. The client device may obtain this data and store the category for the record in memory.

As described above, the respective devices may each contribute to enabling a categorization of a sensitive data field in such a way that the client device is not required to disclose the classification method, the data provider device is not required to disclose the value of the sensitive data field, and a categorization device is employed that does not need to be fully trusted. The client device may enable the categorization, e.g., by determining the categorization data; the data provider device by determining homomorphic encryptions of differences without decrypting the categorization data; and the categorization device by determining matches between values of the sensitive data field and categories without needing to know which values are matched. Thereby, a categorization system, client device, data provider device, and categorization device are obtained that provide improved protection of sensitive information.

In an embodiment, the dataset comprises electronic medical records. The sensitive data field may comprise a disease classification, e.g., according to the ICD classification. As discussed above, in the setting of medical research, protection of sensitive information both in datasets and in categorizations for using those datasets is particularly salient. However, it is noted that the techniques presented herein can be used for various other kinds of data as well, e.g., sensor measurement histories, location histories, e.g., obtained from a GPS sensor, etcetera.

In an embodiment, determining the categorization data comprises encrypting at least one possible value of the sensitive data field multiple times. By providing multiple encryptions of the same possible value to the data provider device, the client device can hide the exact number of possible values that belong to a category, thus providing improved hiding of the categorization to the data provider. For example, the client device can include duplicates in such a way that each category includes the same number of possible values.

In an embodiment, the client device is further configured to obtain values of one or more additional fields for the record, and store said values for the record in the memory. This way, values for multiple data fields of the record can be obtained in which at least the sensitive data field is categorized.

In an embodiment, the data provider device is further configured to, for a first homomorphic encryption and a second homomorphic encryption of the categorization data having the same category, determine a homomorphic encryption indicative of a difference between a possible value encrypted by the first homomorphic encryption and a possible value encrypted by the second homomorphic encryption. The data provider may provide said homomorphic encryption indicative of a difference to the categorization device. The categorization device may be configured to obtain the homomorphic encryption, and to signal an error if the homomorphic encryption indicates a match of the encrypted possible values.

Because of the encryptions and encodings used to construct the categorization data, the data provider device and categorization device individually may not be able to determine whether the categories provided by the client device include multiple possible values. A category including multiple possible values is desirable, e.g., because it may prevent the client device from learning a value of the sensitive data field because it is the only value that has a certain category. The property of a category including multiple possible values may be called "fairness". Using the homomorphic encryption of the difference outlined above, the data provider device and categorization device may together check that each category of the client device contains a minimal number of sensitive data values, thus helping to guarantee fairness.

In an embodiment, the data provider device is further configured to obtain a coarse categorization of the set of possible values of the sensitive data field. The categorization data may be categorization data for a coarse category of the coarse categorization. The value of the sensitive data field for the record may be comprised in the coarse category of the coarse categorization. This may allow to more efficiently categorize a record known to belong to a coarse category according. For example, it may be prevented to determine or transmit difference encryptions of differences between the value of the record and possible values belonging to other coarse categories. For example, records may be categorized into a category that is a subcategory of the coarse category to which they belong. In effect, this may be seen as a form of bucketing to decrease the number of homomorphic additions performed and/or transmitted.

In an embodiment, the categorization device is configured to count a number of records to which a given category is associated. The categorization device may signal an error if said count is below a predefined threshold. This way, it may be detected whether the records to be obtained by the client device satisfy a k-anonymity property in the sense that each category either does not occur or occurs at least k times. Such k-anonymity may be required in various settings, e.g., as part of data sharing agreements or regulations, e.g. HIPAA 18 identifiers or GDPR pseudonymization. In an embodiment, the categorization device is configured to, if an error is signaled, associate a generalized category to at least each record to which said given category is associated. This way, if k-anonymity is not achieved by the original categorization, a coarser categorization may be obtained that does achieve k-anonymity.

In an embodiment, the categorization device is configured to associate a default category to the record if the value of the sensitive data field for the record does not match a possible value according to an obtained homomorphic encryption. This way, it may be guaranteed that a category is assigned to each record. Moreover, especially if the number of possible values to which the default category is to be assigned is relatively large, using the default category in this way can reduce the size the categorization data and the number of difference encryptions determined and/or transmitted.

Other aspects of the invention include a client method, a data provider method, and a categorization method. Embodiments of the methods may be implemented on a computer as a computer implemented method, or in dedicated hardware, or in a combination of both. Executable code for an embodiment of the method may be stored on a computer program product. Examples of computer program products include memory devices, optical storage devices, integrated circuits, servers, online software, etc. Preferably, the computer program product comprises non-transitory program code stored on a computer readable medium for performing an embodiment of the method when said program product is executed on a computer.

In an embodiment, the computer program comprises computer program code adapted to perform all the steps of an embodiment of the method when the computer program is run on a computer. Preferably, the computer program is embodied on a computer readable medium.

Another aspect of the invention provides a method of making the computer program available for downloading. This aspect is used when the computer program is uploaded into, e.g., Apple's App Store, Google's Play Store, or Microsoft's Windows Store, and when the computer program is available for downloading from such a store.

BRIEF DESCRIPTION OF THE DRAWINGS

Further details, aspects, and embodiments of the invention will be described, by way of example only, with reference to the drawings. Elements in the figures are illustrated for simplicity and clarity and have not necessarily been drawn to scale. In the Figures, elements which correspond to elements already described may have the same reference numerals. In the drawings:

FIG. 7a schematically shows an example of an embodiment of a client method;

FIG. 7b schematically shows an example of an embodiment of a data provider method;

FIG. 7c schematically shows an example of an embodiment of a categorization method;

Figure 1:
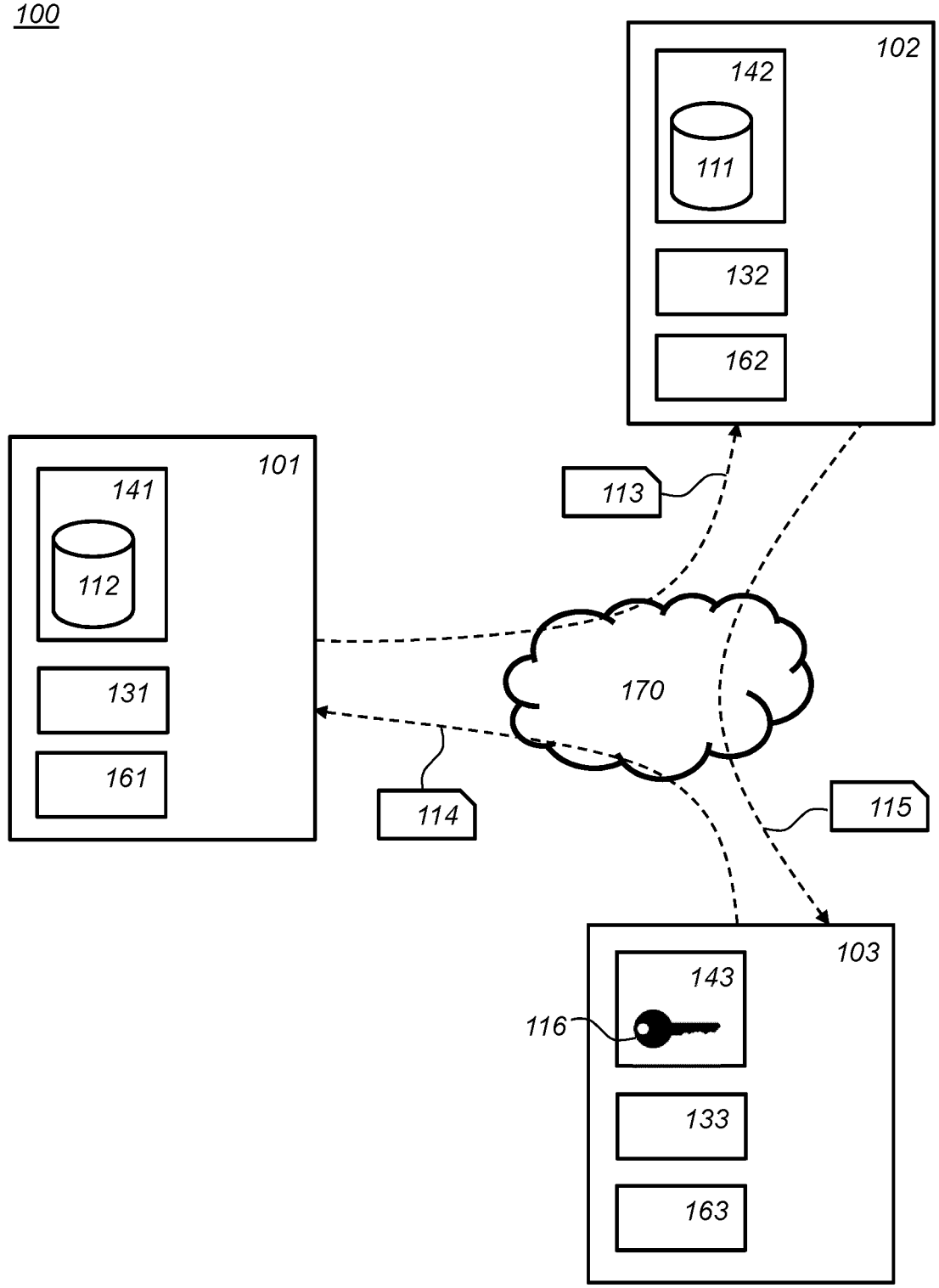
FIG. 1 schematically shows an example of an embodiment of a categorization system.

LIST OF REFERENCE NUMERALS 100, 500, 600 a categorization system
101, 201, 301, 401, 501, 601 a client device
102, 202, 302, 402, 502, 602 a data provider device
103, 203, 303, 403, 503, 603 a categorization device
131, 132, 133 a processor
141, 142, 143 a memory
161, 162, 163 a communication interface
170 a computer network
111, 311, 611 a dataset
112 categories of the sensitive data field
113, 213, 313, 513, 613 categorization data
114, 214, 414 category encodings
115, 315, 415, 615 category encodings and difference encryptions
116, 416, 516 a decryption key
217, 317 values of additional fields
218 categorized records
519 category differences
620 a coarse categorization
221 a categorization
522 an error
231 encoding unit
232 decoding unit
331 providing unit
332, 632 difference unit
431 checking unit
533 fairness encryption unit
534 fairness decryption unit
250, 350, 650 values of the sensitive data field
251 categories
252, 552, 652 encrypted values
253, 253', 353, 453, 453', 553, 553', 653 encoded categories
254, 354, 454, 454' identifiers
255, 355 values of an additional data field
356, 456 difference encryptions
557 category difference encryptions
658, 658' coarse categories
1000 a computer readable medium
1010 a writable part
1020 a computer program
1100 a client device, data provider device, or categorization device
1110 a system bus
1120 a processor
1130 a memory
1140 a user interface
1170 a communication interface
1160 a storage
1161 an operating system
1162, 1163, 1164 instructions

DETAILED DESCRIPTION OF THE EMBODIMENTS

While this invention is susceptible of embodiment in many different forms, there are shown in the drawings and will herein be described in detail one or more specific embodiments, with the understanding that the present disclosure is to be considered as exemplary of the principles of the invention and not intended to limit the invention to the specific embodiments shown and described.

In the following, for the sake of understanding, elements of embodiments are described in operation. However, it will be apparent that the respective elements are arranged to perform the functions being described as performed by them.

Further, the invention is not limited to the embodiments, and the invention lies in each and every novel feature or combination of features described herein or recited in mutually different dependent claims.

Various embodiments relate to categorizing a sensitive data field in a dataset. Such a dataset may comprise one or more records, sometimes also called entries, members, etc. Typically, the dataset comprises multiple such records, e.g., at most or at least 5 records, at most or at least 10 records, at most or at least 100 records, etc. A record may comprise values for one or more data fields. For example, the dataset may be represented as a table, wherein rows of the table represent records; columns of the table represent data fields; and a cell represents a value of a data field for a particular record.

In some embodiments, the dataset comprises electronic medical records. For example, a record may represent a particular patient and a column may represent a piece of medical information concerning that patient, e.g., an attribute of a patient such as an age, a blood group, a length, or a measurement taken by a measurement device such as a blood pressure of the patient. The piece of medical information can also for example relate to a treatment of the patient, e.g., the record may comprise a device parameter of a device used to monitor or treat the patient. However, the techniques described herein are by no means limited to medical data and can be applied to various other types of data, e.g., to other types of records representing personal information, or to device logs, sensor measurements, etc.

Interestingly, at least one of the data fields of dataset may be a sensitive data field. Each record of dataset may comprise a value of the sensitive data field. The sensitive data field may be sensitive in the sense that its exact value should remain hidden to a client device and/or a user of the client device. Despite the sensitivity, the client device and/or its user may be allowed to learn a category of the value of the sensitive data field. For example, learning the category may be sufficient for the purpose at hand of the client device, e.g., in that sense, categorization can enable dissemination of the sensitive data field on a need-to-know basis. The problem of keeping sensitive data hidden is especially salient for medical data, which is by nature privacy-sensitive and whose dissemination is also restricted by various privacy regulations, but applies to various other kinds of data as well.

The categorization may be chosen by the client device, for example, for a particular use of the data. As the inventors realized, it can be desirable not only to hide the values of the sensitive data field to the client device, but also to hide the categorization, e.g., the way in which possible values of the sensitive data field are divided into categories, from other parties such as the data provider holding the dataset or third parties. For example, in this way, a researcher obtaining the dataset for medical research purposes can hide information concerning the kind of research he/she is carrying out. This may stimulate researchers to make use of more data already at an earlier stage in their research. As another example, for a company using a dataset, e.g., to train a machine learning model, the exact type of the data on which the machine learning model is trained may be valuable as intellectual property that the company wants to keep hidden. For these uses and others, it is beneficial if the client device does not need to disclose the exact categorization. In various embodiments, such issues are addressed.

In various embodiments, the sensitive data field represents categorical and/or quantized data, e.g., the set of possible values of the sensitive data field is limited and/or fixed. For example, the number of possible values that the sensitive data field can take on may be at most or at least 10, at most or at least 50, or at most or at least 100. One of the possible values of the sensitive data field may be a value indicative of a missing value for the sensitive data field, e.g., "NULL", "Not a Number" ("NaN"), etc.

For example, the sensitive data field may comprise a disease classification, e.g., according to the ICD classification, International Statistical Classification of Diseases and Related Health Problems. The ICD classification is divided into chapters, which are divided into blocks of three-character categories. Three-character categories may be further subdivided into four-character subcategories and/or using supplementary subdivisions at a fifth or subsequent character level. The sensitive data field may for instance represent a three-character category, a four-character subcategory, and/or a supplementary subdivision of a disease. Another example of a medical classification is LOINC, Logical Observation Identifiers Names and Codes, coding.

As another particular example, the sensitive data field may comprise location information, e.g., a ZIP code, GPS coordinates quantized into location areas, etcetera.

The categorization may map possible values of the sensitive data field into respective categories, e.g., each possible value of the sensitive data field may belong to a single category. In other words, a category may correspond to a set of possible values of the sensitive data field. A category typically comprises multiple possible values of the sensitive data field, e.g., at most or at least 5, or at most or at least 10. For example, each category may comprise multiple possible values. For example, in case the sensitive data field comprises a disease classification, a category may represent a set of possible classifications, e.g., a chapter, a block or a three-character category of the ICD classification. In case of ZIP codes, a sensitive data value may for example be an extended ZIP+4 code whereas its category may be its leading five digits. One of the categories may be a default category, e.g., if no category is assigned explicitly to a possible value of the sensitive value, the value may be considered to belong to the default category. There are typically multiple categories, e.g., at most or at least five, or at most or at least ten.

Apart from the sensitive data field, the dataset may comprise additional data fields. For example, the dataset may comprise one or more additional fields whose values the client device is allowed or intended to learn for a given record. The dataset may also comprise one or more additional fields whose values the client device is not allowed or intended to learn for a given record. The term "sensitive data field" is used throughout in the sense that, at least for a given record, the client device is not allowed to learn the value but is allowed to learn its category. As such, it will be understood that the term does not imply that values for data fields other than the sensitive data field may be freely distributed. For example, the client device may learn values of some additional data fields, but may not further redistribute them. Or, the client device may not learn values of some additional data fields because access to them is so restricted that the client device is not even allowed to learn a categorization. The client device may also not learn values of certain additional data fields because they are not relevant for the purpose at hand.

In various examples described below, only one sensitive data field is used, but it is also possible that each record of the dataset comprises values of multiple sensitive data fields. The techniques described herein may then be used to let the client device learn categories of respective sensitive data fields for a record of the dataset according to respective categorizations.

Throughout this specification, notation $E(x, r)$ may be used to denote homomorphic encryption, e.g., additively homomorphic encryption of a plaintext x using randomness r, e.g., Paillier encryption as disclosed in Pascal Paillier, "Public-key cryptosy stems based on composite degree residuosity classes", Proceedings EUROCRYPT'99 (incorporated herein by reference). Notation $E'(x)$ may be used to denote an encoding of a plaintext x, e.g., a symmetric encryption of the plaintext. Both notations do not explicitly specify the required public and/or secret keys, the use of which will be clear to the skilled person from the context.

FIG. 1a schematically shows an example of an embodiment of a categorization system 100. Categorization system 100 may be for categorizing a sensitive data field in a dataset 111. As also discussed elsewhere, the dataset may comprise one or more records, wherein each record of the dataset may comprise a value of the sensitive data field.

Categorization system 100 may comprise a client device 101 for obtaining the categorization. Categorization system 100 may also comprise a data provider device 102 for providing data to be categorized. Categorization system 101 may also comprise a categorization device 103 for enabling the categorization.

Client device 101 may comprise a processor 131 and a memory 141. Memory 141 may be used for data and/or instruction storage. For example, memory 141 may comprise software and/or data on which processor 131 is configured to act. Memory 141 may be further configured to store obtained categories 112 of the sensitive data field for records of the dataset. Processor 131 may be implemented as one or more processor circuits, e.g. microprocessors, ASICs, FPGA and the like. Memory 141 may comprise computer program instructions which are executable by processor 141. Processor 131, possibly together with memory 141, is configured according to an embodiment of a client device.

Client device 101 may further comprise a communication interface 161 configured to communicate with other devices of categorization system 100 as needed. In particular, client device 101 may communicate with data provider device 102 and/or categorization device 103 as needed. Communication interface 161 may comprise a connector, e.g., a wired connector, e.g., an Ethernet connector, or a wireless connector, e.g., an antenna, e.g., a Wi-Fi, 4G or 5G antenna.

Processor 131 may be configured to determine categorization data 113. Categorization data 131 may comprise, for one or more possible values of the sensitive data field, a homomorphic encryption of the possible value and data encoding a category of the possible value. For instance, the homomorphic encryption may be a probabilistic homomorphic encryption, e.g., using the Paillier or ElGamal cryptosystem, etc. Processor 131 may be further configured to provide categorization data 113 to data provider device 102, e.g., to send categorization data 113 using communication interface 161. Processor 131 may be further configured to obtain from the categorization device 114, e.g., to receive via communication interface 161, data 115 encoding a category of the sensitive data field for a record of the dataset. Processor 131 may be configured to store said category for the record in memory 141.

Data provider device 102 may comprise a processor 132 and a memory 142. Memory 142 may be used for data and/or instruction storage. For example, memory 142 may comprise software and/or data on which processor 132 is configured to act. Memory 142 may also store dataset 111, for example, data provider device 102 may be configured to run a database using memory 142 as memory to store the dataset. Processor 132 may be implemented as one or more processor circuits, e.g. microprocessors, ASICs, FPGA and the like. Memory 142 may comprise computer program instructions which are executable by processor 142. Processor 132, possibly together with memory 142, is configured according to an embodiment of a data provider device.

Data provider device 102 may further comprise a communication interface 162 configured to communicate with other devices of categorization system 100 as needed. In particular, data provider device 102 may communicate with client device 101 and/or categorization device 103 as needed. Communication interface 162 may comprise a connector, e.g., a wired connector, e.g., an Ethernet connector, or a wireless connector, e.g., an antenna, e.g., a Wi-Fi, 4G or 5G antenna.

Processor 132 may be configured to obtain, e.g., receive via communication interface 162, categorization data 113 from client device 101, comprising a homomorphic encryption of a possible value of the sensitive data field and data encoding a category of the possible value. Processor 132 may be further configured to determine, for a record of dataset 111, a homomorphic encryption indicative of a difference between said possible value and a value of the sensitive data field for the record based on the homomorphic encryption of the possible value. Processor 132 may be further configured to provide to categorization device 103, e.g., send via communication interface 162, data encoding the category of the possible value and the homomorphic encryption indicative of the difference, shown together as data 115 in the figure.

Categorization device 103 may comprise a processor 133 and a memory 143. Memory 143 may be used for data and/or instruction storage. For example, memory 143 may comprise software and/or data on which processor 133 is configured to act. Memory 143 may also store a decryption key 116 for homomorphic encryptions, e.g., the homomorphic encryption of the possible value and the homomorphic encryption indicative of a difference between said a possible value and a value of the sensitive data field as discussed above. Typically, this decryption key 116 is not known at least to data provider device 102. Processor 133 may be implemented as one or more processor circuits, e.g. microprocessors, ASICs, FPGA and the like. Memory 143 may comprise computer program instructions which are executable by processor 143. Processor 133, possibly together with memory 143, is configured according to an embodiment of a categorization device.

Categorization device 103 may further comprise a communication interface 163 configured to communicate with other devices of categorization system 100 as needed. In particular, categorization device 103 may communicate with client device 101 and/or data provider device 102 as needed. Communication interface 163 may comprise a connector, e.g., a wired connector, e.g., an Ethernet connector, or a wireless connector, e.g., an antenna, e.g., a Wi-Fi, 4G or 5G antenna.

Processor 133 may be configured to obtain, e.g., receive via communication interface 163, from data provider device 102 data encoding a category of a possible value of the sensitive data field and a homomorphic encryption indicative of a difference between the possible value and a value of the sensitive data field for a record of the dataset, together shown as data 115. Processor 133 may be further configured to determine if the value of the sensitive data field for the record matches the possible value from said homomorphic encryption using the decryption key, and if so, associate said category to the record. Processor 133 may be further configured to provide to client device 101, e.g., send via communication interface 163, data 114 encoding the category associated to the record.

The various devices of categorization system 100, e.g., client device 101, data provider device 102, and/or categorization device 103, may be connected by a computer network 170. The computer network may be an internet, an intranet, a LAN, a WLAN, etc. The computer network may be the Internet. The computer network may be wholly or partly wired, and/or wholly or partly wireless. For example, the computer network may comprise Ethernet connections. For example, the computer network may comprise wireless connections, such as Wi-Fi, ZigBee, and the like. Respective devices may comprise communication interfaces, e.g., communication interfaces 161, 162, and/or 163, which are configured to communicate with other devices of system 100 as needed. Computer network 170 may comprise known elements such as, e.g., a router, a hub, etc. Communication may be in the form of digital messages, e.g., sent and received in electronic form. Computer network 170 may comprise additional devices.

As explained, the various devices of categorization system 100 may enable client device 101 to obtain a categorization for a record of dataset 111 according to categorization data 113 determined by the client device with various advantages, for example, in terms of improved protection of sensitive data. Various particularly advantageous embodiments of the respective devices of system 100 are discussed below.

Figure 2:
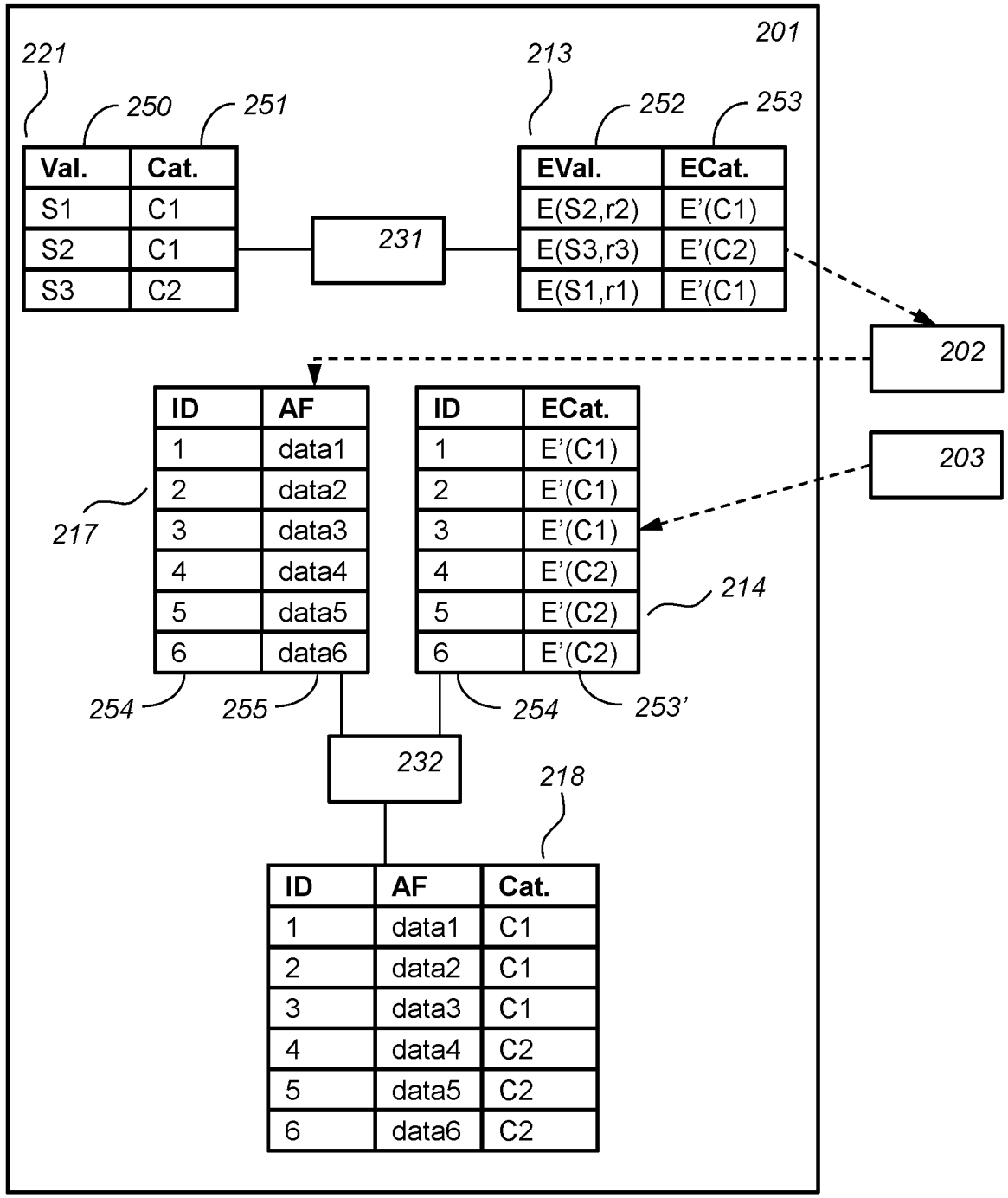
FIG. 2 schematically shows an example of an embodiment of a client device.

FIG. 2 schematically shows an example of an embodiment of a client device 201 for obtaining a categorization of a sensitive data field in a dataset. Client device 201 may be based on client device 101, e.g., client device 201 may comprise processor 131, memory 141, and/or communication interface 161. FIG. 2 schematically shows functional units that may be functional units of a processor of client device 201. For example, FIG. 2 may be used as a blueprint of a possible functional organization of the processor. For example, the functional units shown in FIG. 2, e.g., units 231 and 232, may be wholly or partially be implemented in computer instructions that are stored at device 201, e.g., in an electronic memory of device 201 (not shown), and are executable by a microprocessor of device 201 (not shown). In hybrid embodiments, functional units are implemented partially in hardware, e.g., as coprocessors, and partially in software stored and executed on device 201. For the purpose of explication, FIG. 2 shows various elements that may be stored by client device 201, at various stages of its operation. FIG. 2 also shows various communication patterns, as indicated by dashed lines between client device 201 and a data provider device 202 and categorization device 203.

Shown in the figure is a categorization 221. Categorization 221 may map possible values of sensitive data field 250 to categories 251. Categorization 221 is here visualized as a table mapping possible values "Val.", 250, to respective categories "Cat.", 251. In this example, values "S1" and "S2" are mapped to category "C1" and value "S3" is mapped to category "C2". The example given here is purely for explanatory purposes, for example, there are usually more than three possible values and more than two possible categories. Moreover, usually any given category comprises multiple values, unlike category "C2" in the figure, and in fact, this may be even be required in the system. Still, the present example will be used to explain various aspects.

Client device 201 may obtain categorization 221 in various ways. For example, categorization 221 may be hardcoded, or may be entered by a user. Client device 201 may also determine categorization 221 based on a previous categorization, e.g., by generalizing and/or specializing at least part of the previous categorization, e.g., based on categories that were previously obtained according to the previous categorization. For example, in some embodiments, client device 201 is configured to obtain categories for records in order to train a machine learning model. In such cases, the machine learning training may indicate that more detailed categories for the sensitive data field are needed or less detailed categories suffice, in response to which categorization 221 may be determined accordingly. Categorization 221 may be stored, e.g., in a memory of client device 201. Storing categorization 221 may be performed in various ways, e.g., by a function mapping possible values of the sensitive data field to categories, by a table providing categories for one or more possible values as shown in the figure, by a table enumerative possible values of one or more categories, etcetera.

Client device 201 may comprise an encoding unit 231. Encoding unit 231 may be configured to determine categorization data 213. Categorization data 213 may comprise, for one or more possible values 250 of the sensitive data field, a homomorphic encryption 252 of the possible value and data 253 encoding a category of the possible value. For example, as shown in the figure, categorization data 213 may comprise such a homomorphic encryption and encoding for each possible value of categorization 221. Categorization data 213 may also indicate which data field of the dataset is the sensitive data field.

As is known in the art, a homomorphic encryption is a type of encryption that allows to perform an operation on one or more ciphertexts that results in a corresponding operation on the underlying plaintexts. For example, multiplying two ciphertexts may lead to an encryption of the sum of the plaintext. Interestingly, the homomorphic operations can be performed without using the decryption key, enabling parties to perform operations on ciphertexts without needing, or even being able to, decrypt them. The operations may use the public key of the homomorphic encryption scheme. In the case of client device 201, the public key may be hardcoded in the device, obtained from the categorization device, etc. Homomorphic encryptions are typically probabilistic, in the sense that the encryption operation takes randomness as input and, as a consequence, the same plaintext can result in different ciphertexts.

In various embodiments, the homomorphic encryption is an additively homomorphic encryption allowing an addition operation to be performed on two ciphertexts that results in an encryption of the sum of the corresponding plaintexts. For example, decryption D of an encryption E of a first message m1 using first randomness r1 to combined with an encryption of a second message m2 using second randomness r2 may return m1+m2, e.g., $D(E(m1,r1) \cdot E(m2,r2))=m1+m2$. Additively homomorphic encryption may also allow to homomorphically obtain an encryption of a plaintext multiplied with a known value. For example, decryption D of an encryption E of a message m using randomness r that is homomorphically multiplied by k leads to km, e.g., $D(E(m,r)^k)=km$. An additively homomorphic encryption may be re-randomized by performing addition with an encryption of zero, e.g., resulting in an encryption of the same value that without the decryption key cannot be recognized as being an encryption of the same value. Various known homomorphic encryptions can be readily applied in categorization systems described herein, e.g., Paillier encryption or additively homomorphic ElGamal encryption.

The homomorphic addition may be a modular addition, e.g., plaintexts may be integers modulo a prime number, an RSA modulus, etc. When referring to a "difference" between two values encrypted with additively homomorphic encryption, in this case, the difference according to this modular addition is meant. The homomorphism does not need to be addition, e.g., also multiplicatively homomorphic encryption schemes like multiplicative ElGamal may be used. In such cases, it is understood that the "difference" is with respect to the applicable homomorphic operation, e.g., in case of a multiplicative homomorphism, it refers to the quotient. The homomorphic encryption may support additional operations, e.g., the homomorphic encryption can be a partially homomorphic encryption or a fully homomorphic encryption.

For example, shown in the figure is homomorphic encryption $E(S2, r2)$ of possible value S2, homomorphic encryption $E(S3,r3)$ of possible value S3, and homomorphic encryption $E(S1,r1)$ of possible value S1. The homomorphic encryptions in this example are encrypted with randomness ri that is preferably unpredictable to data provider device 202. This way, data provider device 202 cannot determine which possible values are encrypted by the homomorphic encryptions based on predicting the randomness. For example, respective randomness may be mutually different and randomly generated.

Also shown in the figure are encodings E'(C1), E'(C2), E'(C1) of the categories of respective possible sensitive values S2, S3, S1. Various types of encodings may be used. For example, encoding unit 231 may obtain a symmetric key, e.g., an AES key, and determine the encodings as symmetric encryptions using the symmetric key. In this case, data provider device 202 and/or categorization device 203 preferably do not have access to the symmetric key. Encoding unit 231 may also generate an arbitrary encoding, e.g., generate a random value, for each possible value and store the possible values and respective encodings. Generally, client device 201 is able to determine the possible value associated to an encoding but data provider device 202 and categorization device 203 cannot. This way, devices 202, 203 may assign encodings of categories to records of the dataset without necessarily knowing to which category the record is assigned based on this encoding.

In various embodiments, the encoding is a deterministic encoding, e.g., the same encoding is always used to encode a category, e.g., AES is used with a fixed initialization vector. For example, E'(C1) associated to E(S2,r2) and E'(C1) associated to E(S1,r1) are the same. However, this is not needed and in various embodiments, randomized encodings are used, e.g., a hash with a random nonce. For example, deterministic encodings may help to check fairness, as discussed with respect to FIG. 5, and/or k-anonymity, as discussed with respect to FIG. 4. On the other hand, using a probabilistic encoding may decrease the amount of information learned by the data provider, e.g., in terms of number of categories and their sizes.

In some embodiments, encoding unit 231 may be configured to shuffle, e.g., randomly order, the one or more homomorphic encryptions and their associated category encodings of categorization data 213. For example, in FIG. 2, value S1 and its category C1 occur first in categorization 221 but third in categorization data 213. The inventors realized that, without shuffling, the data provider device 202 may be able to derive information from the ordering of categorization data 213, e.g., especially in case of deterministic encodings of the categories, the locations in which the same encoded category occurs may leak information about the categorization 221. Advantageously, shuffling prevents such information from leaking.

In some embodiments, encoding unit 231 may encrypt at least one possible value of the sensitive data field multiple times. For example, for possible value S3 with category C2, encoding unit 231 may include entry E(S3, r3), E' (C2) using randomness r3 in categorization data 213 but also entry E (S3, r3'), E' (C2) using randomness r3' (not shown). This way, the exact number of possible values that are mapped to the category of the at least one possible value may be hidden from data provider device 202 and/or categorization device 203. For example, encoding unit 231 may encrypt possible values multiple times in such a way that multiple categories occur the same number of times in categorization data 213, decreasing the amount of information that data provider device 202 and/or client device 203 learn about the categorization. For example, if it may be suspected that client device 201 may use a category of five possible values, then by encrypting one or more possible values if the category multiple times, the client device makes it harder for the other devices to confirm this suspicion.

Optionally, encoding unit 231 may include an encoding of a default category in categorization data 213. For example, such a default category may be for associating to a record in case none of the encrypted possible values match the value the sensitive data field for that record. For example, the default category may include relatively many rare possible values, e.g., encoding unit 231 may determine the default category as a category that occurs for a largest number of possible values in categorization 221. By including an encoding of a default category, the need is alleviated for categorization data 213 to include separate entries for possible values of the sensitive data field belonging to the default category, reducing the amount of data that is processed and/or transmitted.

Having determined categorization data 213, client device 201 may be configured to provide the categorization to data provider device 202.

Client device 201 may further comprise a decoding unit 232. Decoding unit 232 may be configured to obtain from categorization device 203 data encoding a category of the sensitive data field for one or more records of the dataset. The data encoding the category typically corresponds to category encodings 253 or is at least derived from it, e.g., as an encryption, a hash, etc. Decoding unit 232 may determine the one or more categories encoded by category encoding data 247, and store the categories for the respective records in a memory of the client device, for example, in a table 218 of categorized records. For example, client device 201 may receive category encoding data 247 for one or more particular records requested by client device 201, for one or more records satisfying a condition specified by the client device, for each record of the dataset, etc. As shown in the figure, client device 201 may obtain identifiers 254 associated to category encoding data 247 and store such identifiers along with the categories in table 218.

Optionally, decoding unit 232 is further configured to obtain values 255 of one or more additional fields for the record. Typically, client device 201 receives these values from data provider device 202. For example, client device 201 may include a request to provide values for the one or more additional fields along with categorization data 213 sent to the data provider device. Decoding unit 232 may store the received values 255 for the record in the memory, e.g., associated with the obtained category. For example, as shown in the figure, decoding unit 232 may obtain identifiers 254 of the records along with the values of the additional data fields and use these to link the received encoded categories 253 to the received values 255 and/or to store the values in memory, e.g., in a table 218 as shown in the figure.

In some embodiments, client device 201 is configured to further train a machine learning model based on the obtained categorization of the sensitive data field for one or more records and/or the values of additional data fields of the records. For example, client device 201 may include the categories and the values of the additional data fields in a training dataset and/or test dataset to train a machine learning model on. For example, the machine learning model maybe a classifier such as an SVM, a clustering algorithm such as k-means, etcetera. Using the techniques herein, the client device may be able to obtain more information about the records for training the model than it would if no information about the sensitive data field could be disclosed at all. This way, an overall better machine learning model may be obtained. In similar embodiments, client device 201 is configured to perform a hypothesis test based on the obtained categorization, e.g., to test whether the categories of the sensitive data field correlate to values of another field of the dataset, thereby allowing to perform research, e.g., medical research, without needing to disclose the hypothesis being tested.

Figure 3:
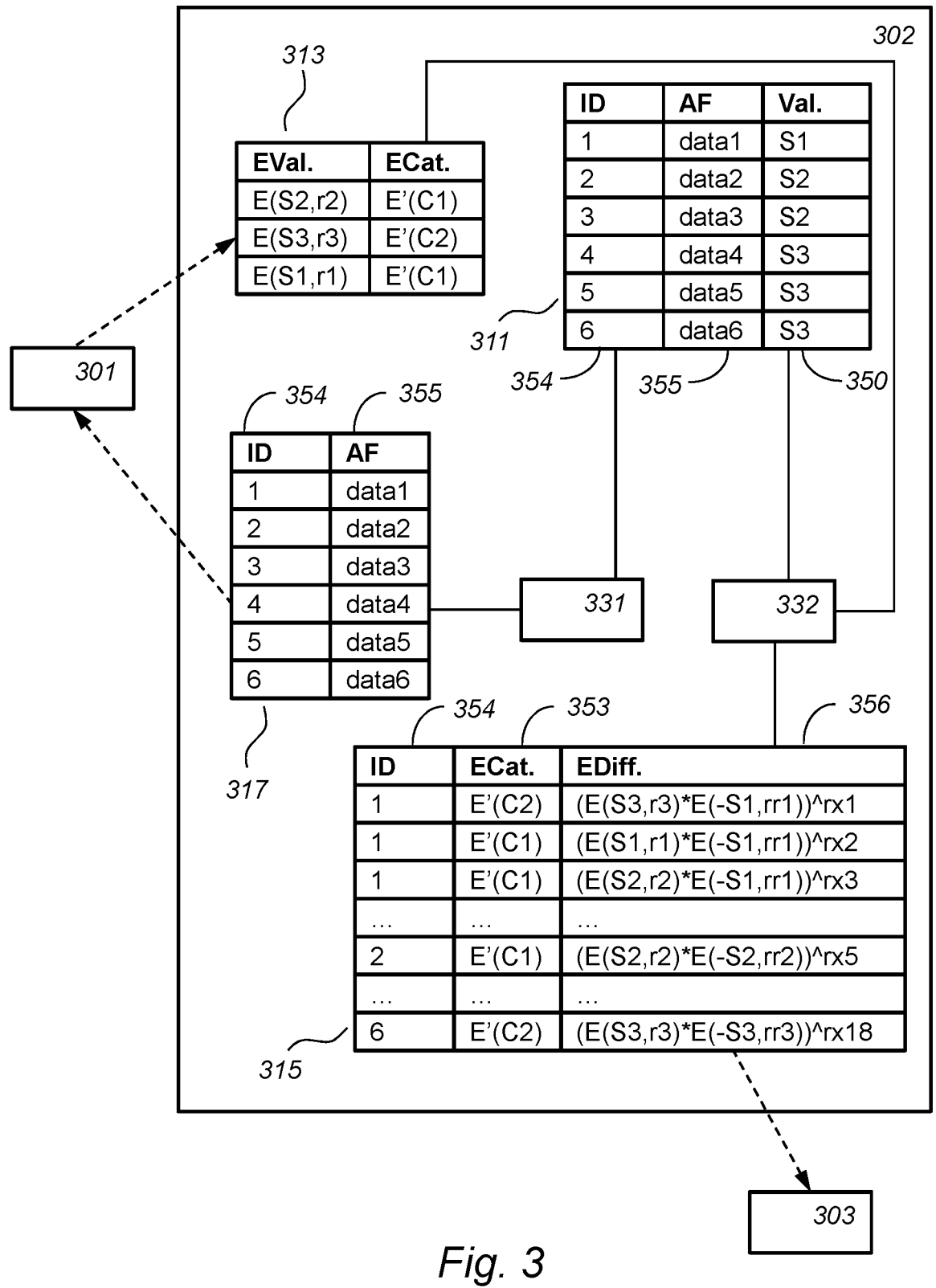
FIG. 3 schematically shows an example of an embodiment of a data provider device.

FIG. 3 schematically shows an example of an embodiment of a data provider device 302 for providing data for categorizing a sensitive data field in a dataset 311. Data provider device 302 may be based on data provider device 102, e.g., data provider device 302 may comprise processor 132, memory 142, and/or communication interface 162. FIG. 3 schematically shows functional units that may be functional units of a processor of data provider device 302. For example, FIG. 3 may be used as a blueprint of a possible functional organization of the processor. For example, the functional units shown in FIG. 3, e.g., units 331 and 332, may be wholly or partially be implemented in computer instructions that are stored at device 302, e.g., in an electronic memory of device 302 (not shown), and are executable by a microprocessor of device 302 (not shown). In hybrid embodiments, functional units are implemented partially in hardware, e.g., as coprocessors, and partially in software stored and executed on device 302. For the purpose of explication, FIG. 3 shows various elements that may be stored by data provider device 302, at various stages of its operation. FIG. 3 also shows various communication patterns, as indicated by dashed lines between data provider device 302 and client device 301 and categorization device 303.

Shown in the figure is dataset 311. Dataset 311 may comprise one or more records. Shown in this figure are six records. Each record of dataset 311 may comprise a value "Val.", 350 of the sensitive data field. As discussed, records may also comprise values of additional fields, e.g., in this example, a single additional field "AF", 355, is shown. In this example, each record is associated to an identifier "ID", 354, in this case, numbered from 1 to 6. The first record has identifier 1, value "data1" for the additional data field, and value "S1" for the sensitive data field, and similarly for the other records. Data provider device 302 may be configured to store dataset 311 in any suitable way, e.g., as an array in memory, as a table of a database, etcetera.

Data provider device 302 may be configured to obtain categorization data 313 from client device 301. Categorization data 313 may comprise a homomorphic encryption "EDiff.", 356, of a possible value of the sensitive data field and data encoding a category of the possible value, for example, multiple such encryptions and respective encodings. Categorization data 313 may also comprise an encoding of a default category. As shown in the figure, categorization data 313 may correspond to categorization data 213 determined by client device 201.

Data provider device 302 may further comprise a difference unit 332 configured to determine, for a record of the dataset, a homomorphic encryption indicative of a difference between a possible value of the sensitive data field and a value of the sensitive data field for the record, based on the homomorphic encryption of the possible value comprised in categorization data 313. For example, the encryption may be an encryption of zero if the difference is zero, e.g. if the value of the sensitive data field is equal to the possible value, and of a nonzero value if the difference is not zero, e.g., if the value of the sensitive data field is not equal to the possible value. This may enable a party decrypting the homomorphic encryption, e.g., categorization device 303, to determine whether the value and possible value used to determine the encryption are equal, and hence, whether the value belongs to the category corresponding to the possible value. That party may do this without needing to know the actual values themselves. At the same time, also data provider device 302 does not typically know the what the possible value is, since it remains encrypted. Hence, the homomorphic encryption helps to determine whether the record belongs to the category of the possible value, with improved secrecy of the categorization and/or dataset.

In some embodiments, difference unit 332 is configured to determine the homomorphic encryption by determining an encryption of the difference between the possible value, e.g., S2, and the value, e.g., S1. For example, difference unit 332 may encrypt a negation of the value, e.g., encryption $E(-S1, rr1)$ for value S1 with randomness rr1; and homomorphically add this encryption to the encryption of the possible value, e.g., $E(S2, r2)$.

Although the resulting encryption, e.g., $E(S2, r2)*E(-S1, rr1)$, could already be used by categorization device 303, difference unit 332 may beneficially additionally randomize the value encrypted by the resulting encryption, e.g., by homomorphically multiplying it with a random value, e.g., rx2, e.g., obtaining $(E(S2, r2)*E(-S1,rr2))$ rx2. In this example, an encryption may be obtained of either zero, in case the possible value S2 is equal to the actual value S1, or of a random value $rx2 \cdot (S2-S1)$, in case the possible value S2 does not equal the actual value S1. This has as an advantage that categorization device 303 does not learn difference S2−S1 which gives information about the dataset and/or categorization used.

More generally, this advantage can be obtained by determining an encryption of which the plaintext is random if the possible and actual values are not equal and fixed if the values are equal. This can be done in various ways. For example, difference unit 332 may multiply value S1 by random value rx2 and encrypt it, homomorphically multiply encryption $E(S2, r2)$ by −rx2 and homomorphically add the two to obtain $E(S2, r2)^{-rx2}*E(S1 \cdot rx2, rr1)$, which may encrypt $S2 \cdot -rx2+S1 \cdot rx1=(S1-S2)$ rx2. Difference unit 332 may also add an encryption of a constant to the encryption, e.g., so that the plaintext being equal to that constant indicates equality. Various alternatives will be apparent to the skilled person, including alternatives in which other homomorphisms are used, e.g., a multiplicative homomorphism.

In an embodiment, difference unit 332 is configured to determine a homomorphic encryption indicative of a difference between a possible value and a value for a record for each possible value comprised in categorization data 313. This may enable to fully categorize the value for the record according to the categorization. In this case, difference unit 332 may use the same encryption of the value for the record, or its negation, for determining for multiple homomorphic encryptions of respective differences, thus improving performance. In an embodiment, difference unit 332 is configured to determine a homomorphic encryption indicative of a difference for each combination of a possible value comprised in categorization data 313 and each value 350 of a record in dataset 311, thus enabling categorization of each record of the dataset 311.

Difference unit 332 may be further configured to provide, to categorization device 303, data 353 encoding the category of the possible value and homomorphic encryption 356 indicative of the difference. For example, such a category encoding and homomorphic encryption may form an entry in a table, as illustrated in the figure as table 315 with category encodings "ECat.", 353, as a column and homomorphic encryptions "EDiff.", 356, as another column. The table may also include an identifier 354 of the record corresponding to the entry.

The encoding of the category may be the same encoding used in categorization data 313, although it is also possible to further encode the value, e.g., apply a hash function to it, as long as client device 301 can determine which category is encoded. The homomorphic encryption may be as described for client device 201.

In an embodiment, for a record, data encoding the category of a possible value and a corresponding homomorphic encryption may be provided for each possible value of categorization data 313, enabling categorization of the record. For example, table 315 shows entries for record 1 combined with each possible value of categorization data 313.

Interestingly, the order in which entries for a record are provided does not have to coincide with the order of categorization data 313, e.g., difference unit 332 may be configured to shuffle the entries, thus reducing the amount of information about dataset 311 that categorization device 303 can learn.

In an embodiment, the data encoding the category and the homomorphic encryption may be provided for each combination of a record of dataset 311 and a possible value of categorization data 313, enabling categorization of the dataset. This is illustrated in table 315 showing encoded categories "ECat.", 353 and difference encryptions "EDiff.", 356 for each combination of a record of dataset 311 and a possible value of categorization data 313. Again, difference unit 332 may shuffle the entries per record, e.g., separately for each record, thus reducing the amount of information about dataset 311 that categorization device 303 can learn.

For example, the first entry of table 315 shows encoded category E'(C2) and homomorphic encryption $(E (S3, r3)*E(-S1, rr1))^{rx1}$. The homomorphic encryption may be constructed based on homomorphic encryption $E(S3, r3)$ of possible value S3 and based on value S1 of the first record of dataset 311. In this case, the homomorphic encryption may encrypt value $(S3-S1) \cdot rx1$, indicating that the value of the sensitive data field for the first record of dataset 311 does not correspond to the second possible value of categorization data 313. Hence, this entry of table 315 may suggest not to assign the encoded category C2 to this record.

As another example, the second entry of table 315 shows encoded category E'(C1) and homomorphic encryption $(E(S1, r1)*E(-S1, rr1))^{rx2}$. The homomorphic encryption may be constructed based on homomorphic encryption $E(S1, r1)$ of possible value S1 and based on value S1 of the first record of dataset 311. In this case, the homomorphic encryption may encrypt value $(S1-S1) \cdot rx2=0$, indicating that the value of the sensitive data field for the first record of dataset 311 corresponds to the third possible value of categorization data 311. Hence, this entry of table 315 may suggest to assign the encoded category C1 to this record.

In an embodiment, data provider device 302 further comprises a providing unit 331 configured to provide values 355 of one or more additional fields for a record being categorized, e.g., for each record of table 315. For example, providing unit 331 may obtain a selection of additional fields to be provided, e.g., from the client device. Thereby, a more complete version of the record can be obtained by the client device. As illustrated, identifiers 354 may be used to link the values for the additional data fields to the records.

Figure 4:
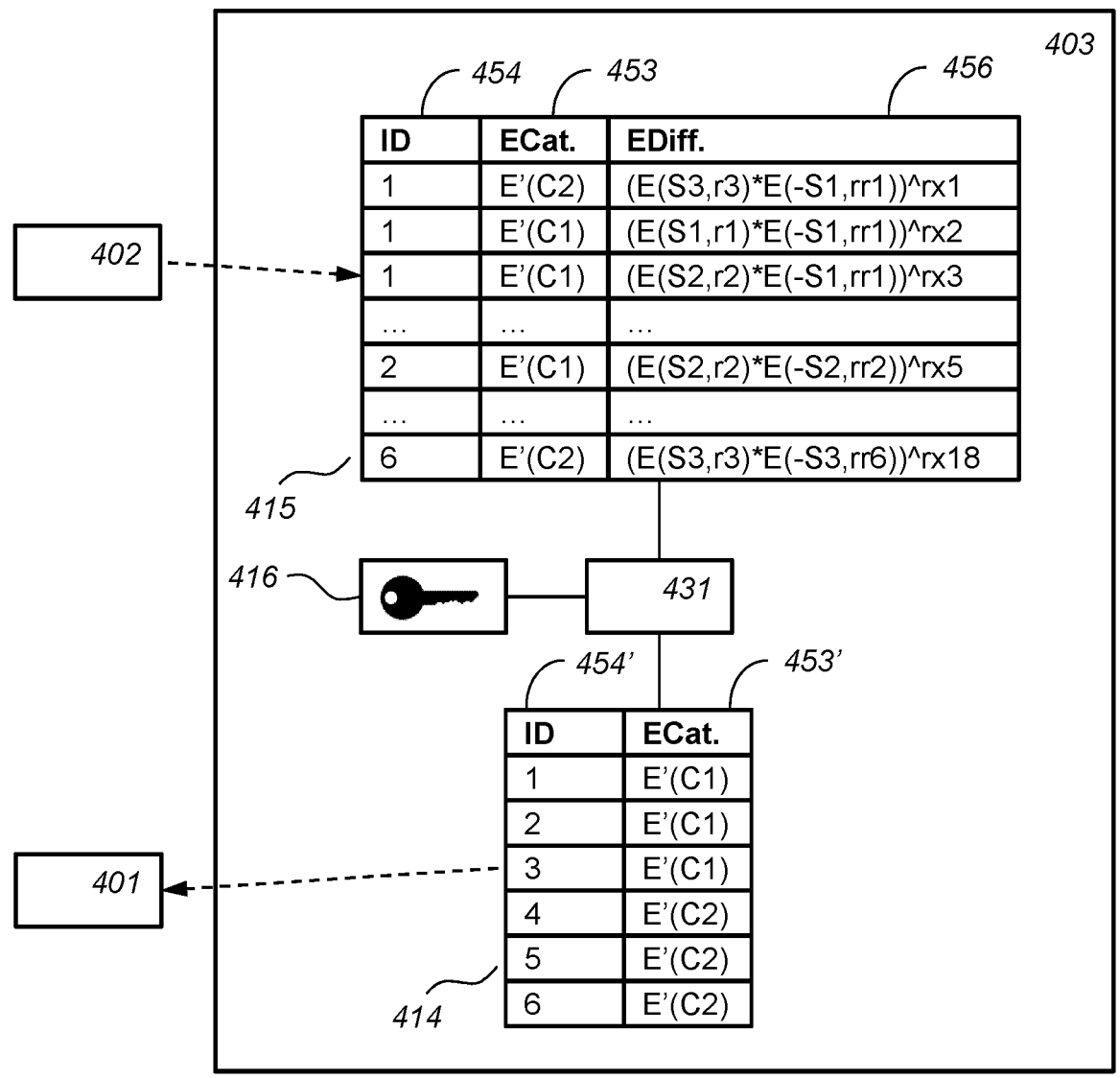
FIG. 4 schematically shows an example of an embodiment of a categorization device.

FIG. 4 schematically shows an example of an embodiment of a categorization device 403 for enabling a categorization of a sensitive data field in a dataset. Categorization device 403 may be based on categorization device 103, e.g., categorization device 403 may comprise processor 133, memory 143, and/or communication interface 163. FIG. 4 schematically shows functional units that may be functional units of a processor of categorization device 403. For example, FIG. 4 may be used as a blueprint of a possible functional organization of the processor. For example, the functional units shown in FIG. 4, e.g., unit 431, may be wholly or partially be implemented in computer instructions that are stored at device 403, e.g., in an electronic memory of device 403 (not shown), and are executable by a microprocessor of device 403 (not shown). In hybrid embodiments, functional units are implemented partially in hardware, e.g., as coprocessors, and partially in software stored and executed on device 403. For the purpose of explication, FIG. 4 shows various elements that may be stored by categorization device 403, at various stages of its operation. FIG. 4 also shows various communication patterns, as indicated by dashed lines between categorization device 403 and client device 401 and data provider device 402.

Categorization device 403 may be configured to obtain, from data provider device 402, data encoding a category of a possible value of the sensitive data field and a homomorphic encryption indicative of a difference between the possible value and a value of the sensitive data field for a record of the dataset. Categorization device 403 may receive multiple such entries comprising such a category encoding and such a difference encryption, as illustrated in the figure by table 415 comprising such entries. For example, table 415 may correspond to table 315 discussed elsewhere. Table 415 may comprise encoded categories "ECat.", 453 and difference encryptions "EDiff.", 456. Table 415 may also include identifiers "ID", 454, of the respective records to which the table entries apply.

Categorization device 403 may comprise a checking unit 431. Given an encoding of a category and a homomorphic encryption of a difference for a record, e.g., as described above, checking unit 431 may be configured to determine if the value of the sensitive data field for the record matches the possible value from the homomorphic encryption using decryption key 416. Decryption key 416 may be a decryption key corresponding to the homomorphic encryptions used, e.g., in categorization data 113, 213, 313 and/or difference encryptions 356, 456. For example, checking unit 431 may decrypt a homomorphic encryption 456 and check whether it corresponds to zero or another fixed value indicating that the value of the sensitive data field is equal to the possible value. Various homomorphic encryption schemes have been mentioned, e.g., Paillier encryption, and their decryption procedures as known from the art may be employed. Categorization device 403 typically performs such a check for each received entry comprising a category and homomorphic encryption.

If the values match, checking unit 431 may associate the category to the record. For example, checking unit 431 may construct a table 414 of record identifiers 454' and associated encoded categories 453'. The encoded categories of the table 414 typically correspond to the encoded categories 453 obtained from the data provider device 402, although a further encoding, e.g., a hash or similar, may be applied. Optionally, checking unit 431 may, once it has associated an encoded category to a record, skip subsequent homomorphic encryptions corresponding to the same record, hence decreasing use of computational resources.

For example, in the example shown in the figure, checking unit 431 may decrypt homomorphic encryption $(E(S3, r3)*E(-S1,rr1))^{rx1}$ of the first entry of table 415 and find that it encrypts nonzero value $(S3-S1)\cdot rx1$. Based on this, checking unit 431 may not associate encoded category E' (C2) to record 1 at this point. Proceeding to the second entry, checking unit 431 may decrypt homomorphic encryption $(E(S1, r1)*E(-S1, rr1))^{rx2}$ and find that it encrypts $(S1-S1)\cdot rx2=0$. Based on this, checking unit 431 may associated encoded category E'(C1) of this entry to record 1. Checking unit 431 may now skip the third entry of table 415 since it relates to the same record and proceed to the fourth record, etcetera.

Optionally, checking unit 431 is configured to associate a default category to a record if the value of the sensitive data field for the record does not match a possible value according to an obtained homomorphic encryption. For example, the default category or its encoding may be hardcoded, or checking unit 431 may obtain it from client device 401 or data provider device 402. For example, checking unit 431 may assign the default category to each record when first encountering the record identifier in table 415 and then overwrite the category based on determining a match, or similar. Hence, checking unit 431 may assign a category at least to each record for which at least one entry occurs in table 415.

In some embodiments, checking unit 431 is configured to count a number of records to which a given category is associated; and to signal an error if said count is below a predefined threshold k. In an embodiment, checking unit 431 may signal the error only if the count is nonzero. When counting numbers of records with a given category, category encodings 453 are preferably deterministic, e.g., all encodings of the same category are the same. Checking unit 431 can for instance scan through table 414 to count the number of records to which a given category is associated. If the error is signaled, this may indicate that the so-called k-anonymity property is not satisfied for the categorization of the dataset. k-anonymity is a commonly used measure of whether a dataset is sufficiently anonymized, hence, checking it may increase the guarantee that the categorization provides sufficient anonymization. The value of k may for instance be predefined or provided by the data provider device 402. Categorization device 431 may be configured to, if the error is signalled, not provide the data 414 encoding the categories to client device 401.

In some embodiments, if the error is signalled for a present category, checking unit 431 is configured to associate a generalized category to at least each record to which the present category is associated. Checking unit 431 may in such case merge the category with one or more other categories such that the generalized category reaches the threshold, e.g., by associating each record of the present category and the other categories to the generalized category. As an encoding of the generalized category, for example, a combination of the encodings of the combined categories can be used, e.g., a concatenation, a homomorphic addition of the categories in case they are encrypted using a homomorphic encryption scheme, etcetera.

Checking unit 431 may determine which other categories to combine with the present categories by selecting categories such that the threshold is met. Checking unit 431 may also combine the present category with a default category, for instance. Checking unit 431 may also obtain data indicating how to generalize categories, e.g., from the client device 401, e.g., indicating a hierarchy of encoded categories, wherein checking unit 431 generalizes a category to its parent category together with other categories with the same parent. For example, in the case of categorizing medical records, such a hierarchy may be according to the hierarchy of ICD classifications or LOINC codes.

In any case, if the generalized category still does not meet the threshold, checking unit 431 may perform additional generalizations. Thus, checking unit 431 may generalize categories in such a way that each category that is associated to at least one record, has a number of records assigned to it that is at least equal to the threshold.

Checking unit 431 may be configured to provide, to the client device 401, data encoding the category associated to the record, e.g., for each record of table 415. For example, checking unit 431 may provide a table 414 of identifiers and encoded categories to client device 401, or checking unit 431 may simply provide a category encoding or sequence of category encodings, e.g., in case the client device knows in which order the category encodings are sent.

Figure 5:
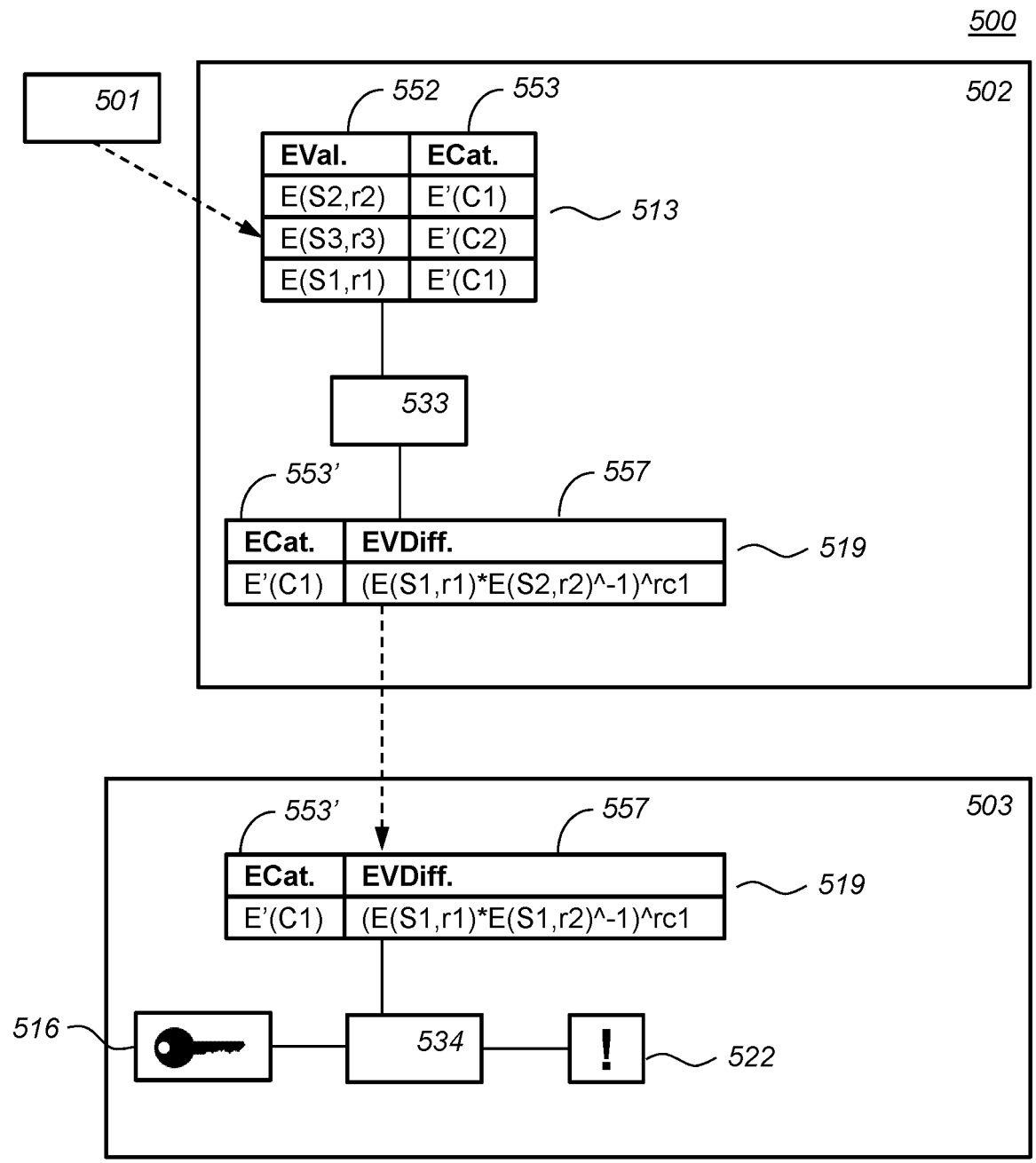
FIG. 5 schematically shows an example of an embodiment of a categorization system.

FIG. 5 schematically shows an example of an embodiment of a categorization system 500. Categorization system 500 comprises at least a data provider device 502, e.g., based on data provider device 102 or 302 and a categorization device 503, e.g., based on categorization device 103 or 403. Also shown in the figure is a client device 501, e.g., based on client device 101 or 201. As in FIG. 2-FIG. 4, this figure schematically shows functional units of the respective devices and various elements that may be stored at the respective devices.

Shown in the figure is categorization data 513 obtained by the data provider device 502 from a client device 501. For example, for one or more homomorphic encryptions 552 of possible values of the sensitive data field, categorization data 513 provides encodings 553 of categories for the respective possible values. Since homomorphic encryptions 552 are typically probabilistic, data provider device 502 may not be able to check whether different entries of categorization data 513 actually correspond to different possible values. For example, although categorization data 513 may comprise a number of different encryptions with the same encoded category, it could be the case that each of these encryptions is an encryption of the same possible value. In such a case, the client device can learn the exact value of the sensitive data field for this category since the category effectively has size one. Moreover, categorization device 503 typically does not obtain the categorization data, so also the categorization device may not be able to check whether different entries of the categorization data correspond to different possible values. The guarantee that categories are sufficiently large may be referred to as a "fairness" property.

To provide improved guarantees that categories are sufficiently large, data provider device 502 depicted in FIG. 5 comprises a fairness encryption unit 533. Fairness encryption unit 533 may be configured to, for a first homomorphic encryption and a second homomorphic encryption of categorization data 513 having the same category, determine a homomorphic encryption indicative of a difference between a possible value encrypted by the first homomorphic encryption and a possible value encrypted by the second homomorphic encryption. Similarly to homomorphic encryptions 356, 456 described above, the encryption may encrypt a fixed value, e.g., zero, if the first and second homomorphic encryptions encrypt the same value, and encrypt a random value if they do not encrypt the same value. For example, given encryptions $E(S1,r1)$ and $E(S2,r2)$ of possible values both having category C1, the difference encryption may be determined as $(E(S1, r1)*E(S2,r2)^{-1})^{rc1}$ with randomness rc1. Various ways of determining difference encryptions have been described with respect to encoding unit 231 may be readily adapted to the present case, including the use of multiplicatively homomorphic encryption or other types of homomorphic encryption.

Fairness encryption unit 533 may for example determine a difference encryption for each pair of homomorphic encryptions having the same encoded category. Preferably, the category encodings are deterministic so that no two different encodings of the same category exist. It is not necessary to take each pair, e.g., fairness encryption unit 533 may take a randomized sample to save computational and/or communication resources.

Fairness encryption unit may be configured to provide the difference encryptions 557, e.g., along with the associated encoded categories 553', as category differences 519 to the categorization device 519.

Categorization device 503 may comprise a fairness decryption unit 534. Fairness decryption unit 534 may be configured to obtain category difference encryptions 519 and to and signal an error 522 if a difference encryption indicates a match of the encrypted possible values. For example, fairness decryption unit 534 may use a decryption key 516, e.g., decryption key 116 or 416, to determine the plaintext of the difference encryption and check whether the plaintext is equal to zero or another value indicating that the homomorphic encryptions encrypt the same possible value of the sensitive data field.

Fairness decryption unit 534 can signal an error if at least one of the received difference encryptions 557 indicates a match; for instance, this way it can be checked that no possible value of the sensitive data field is encrypted twice. Fairness decryption unit 534 can also signal an error only if all received difference encryptions for the same encoded category indicate a match; for instance, in this way it can be checked that each encoded category comprises at least two possible values. Various alternatives can be envisioned, e.g., fairness decryption unit 534 may count the number of different possible values per category and signal an error if the number is below a threshold, etc. If the error is signalled, typically, categorization device 503 does not provide category encodings to the client device 501. Categorization device 503 may also, for example, notify a user or the data provider device 502, etcetera.

Figure 6:
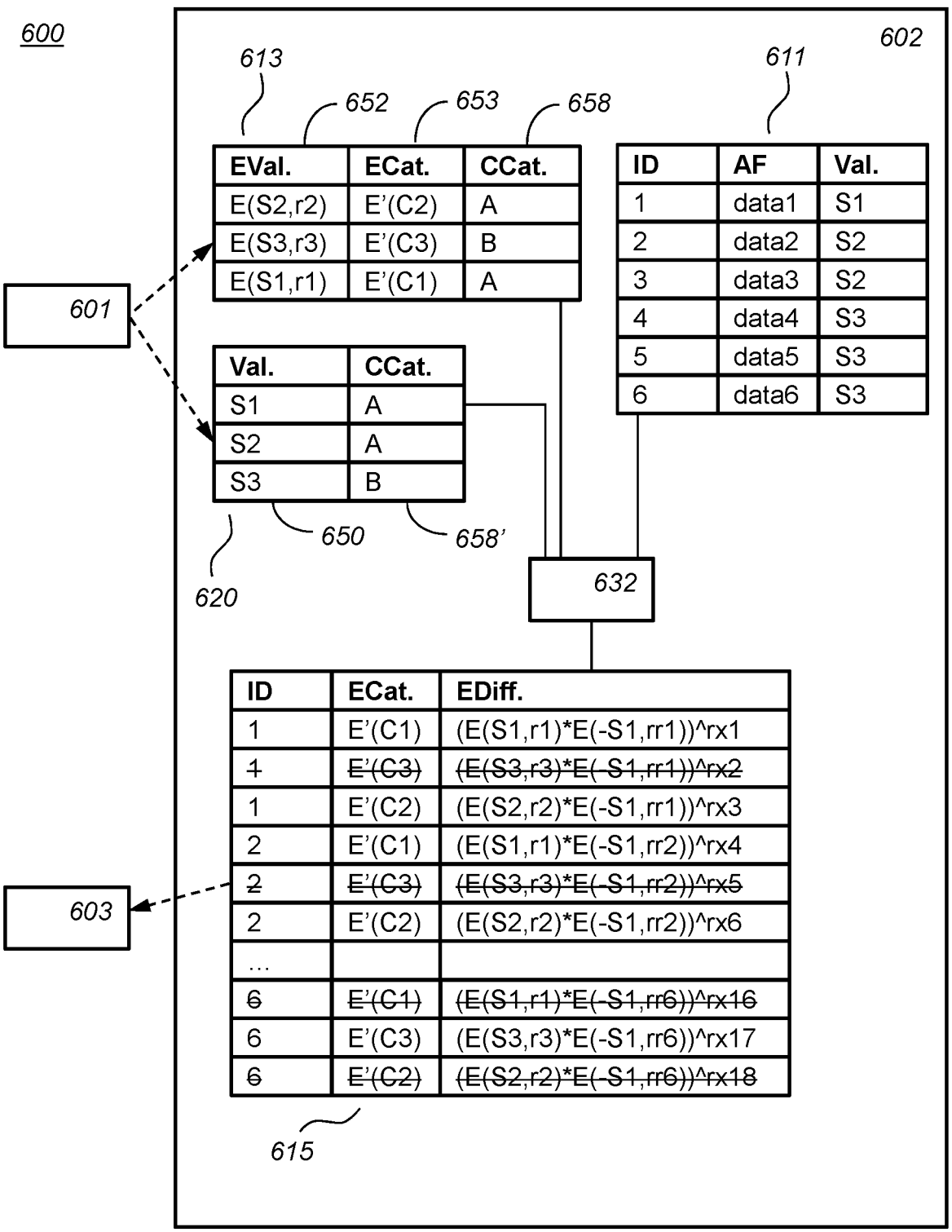
FIG. 6 schematically shows an example of an embodiment of a categorization system.

FIG. 6 schematically shows an example of an embodiment of a categorization system 600. Categorization system 600 comprises at least a data provider device 602, e.g., based on data provider device 102, 302 or 502. Categorization system 600 may also comprise a client device, e.g., based on client device 101 or 201, and/or a categorization device, e.g., based on categorization device 103, 403, and/or 503. As in FIG. 2-FIG. 5, this figure schematically shows functional units of the respective devices and various elements that may be stored at the respective devices.

As shown in the figure, data provider device 602 may comprise a difference unit 632, e.g., based on difference unit 332 of data provider device 302. Given homomorphic encryptions 652 of possible values of the sensitive data field and encodings 653 of their respective encodings, as comprised in categorization data 613, and given a record of dataset 611, difference unit 332 may be configured to determine a homomorphic encryption indicative of a difference between the possible value and the value of the sensitive data field for the record, e.g., as described before.

As discussed for difference unit 332, in order to fully categorize dataset 611, a difference unit may determine such difference encryptions for each combination of a record of the dataset and an encryption of a possible value. This may result in a number of encryptions that scales in the product of the size of the dataset and the number of possible values.

Difference unit 632, however, is configured to obtain a coarse categorization 620 of the set of possible values of the sensitive data field. The coarse categorization may assign a coarse category 658' to each possible value 650 of the sensitive data field in such a way that, if two possible values have the same category according to the regular categorization 613, they also have the same category according to the coarse categorization. Although the regular categorization may be sensitive, the coarse categorization is typically less detailed, so the client device 601 may be willing to disclose the coarse categorization to the data provider device 602.

For example, shown in the figure is a coarse categorization assigning coarse category "A" to possible values "S1" and "S2" and coarse category "B" to possible value "S3". Categorization data 613 assigns category "C1" to possible value "S1", category "C2" to possible value "S2", and category "C3" to possible value "S3". As shown in the figure, client device 601 may provide coarse categorization 620 to data provider device 602 to obtain it. The coarse categorization may also be predetermined, for instance. Apart from providing the coarse categorization 620, client device 601 may also provide coarse categories 658 corresponding to the entries of categorization data 613 for data provider 602 to obtain it.

Difference unit 632 may be configured to determine difference encryptions according to the coarse categorization. In particular, difference unit 632 may determine category encodings and difference encryptions for one or more particular coarse categories, for instance, for each coarse category of the coarse categorization to which a record of dataset 611 belongs. In particular, difference unit 632 may obtain categorization data for a particular coarse category, e.g., by selecting entries of overall categorization data 613 according to coarse categories 658. Difference unit 632 may then determine difference encryptions for records of that coarse category, e.g., a homomorphic encryption of a difference between a possible value and a value of a record for each possible value belonging to the coarse category and each value of a record belonging to the coarse category.

Put in another way, given a record of the dataset 611, difference unit 632 may select those possible values from categorization data 613 that belong to the same coarse category according to coarse categorization 620 and determine difference encryptions for the value of the sensitive data field for that record and those possible values. By way of example, several resulting category encodings and difference encryptions 615 are shown in FIG. 6. For the first record, the value "S 1" belongs to coarse categorization "A", so the first and third entries of categorization data 613 are selected, leading to the first and third entries of table 615. The second entry of categorization data 613 is not selected, as indicated with the stricken through second element of table 615. This element, as other stricken through elements of the able, are typically neither determined nor sent to categorization device and are shown here in the figure for illustration purposes only. As another example, for the sixth record of dataset 611, encrypted possible value E(S3,r3) is considered because this possible value, like value "S3" of the record, belongs to coarse category "B". As highlighted by this example, a considerable saving in the number of encryptions to be determined and/or transmitted can be achieved since for a given record, only possible values with the same coarse category need to be considered instead of all possibilities.

Categorization device 603 may be configured to obtain category encodings and difference encryptions 615 for one or more coarse categories of coarse categorization 603. For each coarse category separately or for multiple coarse categories combined, categorization device 603 may associate categories to records and provide category encodings associated to records to the client device, as described in more detail, e.g., for categorization device 403. Client device 601 may obtain category encodings for each coarse category separately or for multiple course categories combined and store them in memory, as discussed elsewhere. Accordingly, a categorization according to categorization data 613 may be obtained in a more efficient way by making use of coarse categorization 620.

FIG. 7a schematically shows an example of an embodiment of a client method 700. Client method 700 may be for obtaining a categorization of a sensitive data field in a dataset. The dataset may comprise one or more records. Each record of the dataset may comprise a value of the sensitive data field.

Client method 700 may comprise communicating 710 with a data provider device and a categorization device. Client method 700 may further comprise storing 720 categories of the sensitive data field for records of the dataset. Client method 700 may also comprise determining 730 categorization data. The categorization data may comprise, for one or more possible values of the sensitive data field, a homomorphic encryption of the possible value and data encoding a category of the possible value. Client method 700 may comprise providing 740 the categorization data to the data provider device. Client method 700 may also comprise obtaining 750 from the categorization device data encoding a category of the sensitive data field for a record of the dataset, and store said category for the record in the memory.

FIG. 7b schematically shows an example of an embodiment of a data provider method 800. Data provider method 800 may be for providing data for categorizing a sensitive data field in a dataset. The dataset may comprise one or more records. Each record of the dataset may comprise a value of the sensitive data field Data provider method 800 may comprise communicating 810 with a client device and a categorization device. Data provider method 800 may further comprise storing 820 the dataset.

Data provider method 800 may comprise obtaining 830 the categorization data from the client device. The categorization data may comprise a homomorphic encryption of a possible value of the sensitive data field and data encoding a category of the possible value. Data provider method 800 may further comprise determining 840, for a record of the dataset, a homomorphic encryption indicative of a difference between said possible value and a value of the sensitive data field for the record based on the homomorphic encryption of the possible value. The determining may be performed repeatedly, e.g., for each record of the dataset and/or possible value of the sensitive data field. Data provider method 800 may also comprise providing 850, to the categorization device, data encoding the category of the possible value and the homomorphic encryption indicative of the difference.

FIG. 7c schematically shows an example of an embodiment of a categorization method 900. Categorization method 900 may be for enabling a categorization of a sensitive data field in a dataset. The dataset may comprise one or more records. Each record of the dataset may comprise a value of the sensitive data field.

Categorization method 900 may comprise communicating 910 with a client device and a data provider device. Categorization method 900 may also comprise storing 920 a decryption key for homomorphic encryptions. Categorization method 900 may further comprise obtaining 930, from the data provider device, data encoding a category of a possible value of the sensitive data field and a homomorphic encryption indicative of a difference between the possible value and a value of the sensitive data field for a record of the dataset. Categorization method 900 may comprise determining 940 if the value of the sensitive data field for the record matches the possible value from said homomorphic encryption using the decryption key, and if so, associating 941 said category to the record. Steps 940 and/or 941 may be performed repeatedly, e.g., for each received such difference encryption. Categorization method 900 may also comprise providing 950, to the client device, data encoding the category associated to the record.

Many different ways of executing the method are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. For example, steps 710 and 720 of method 700 may be executed, at least partially, in parallel. Moreover, a given step may not have finished completely before a next step is started.

Embodiments of the method may be executed using software, which comprises instructions for causing a processor system to perform method 700, 800, and/or 900. Software may only include those steps taken by a particular sub-entity of the system. The software may be stored in a suitable storage medium, such as a hard disk, a floppy, a memory, an optical disc, etc. The software may be sent as a signal along a wire, or wireless, or using a data network, e.g., the Internet. The software may be made available for download and/or for remote usage on a server. Embodiments of the method may be executed using a bitstream arranged to configure programmable logic, e.g., a field-programmable gate array (FPGA), to perform the method.

It will be appreciated that the invention also extends to computer programs, particularly computer programs on or in a carrier, adapted for putting the invention into practice. The program may be in the form of source code, object code, a code intermediate source, and object code such as partially compiled form, or in any other form suitable for use in the implementation of an embodiments of the method. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth.

In an embodiment, the client device 101 comprises an encoding circuit and a decoding circuit. In an embodiment, the data provider device 102 comprises a providing circuit and a difference circuit. In an embodiment, the categorization device 103 comprises a checking unit. The devices may comprise additional circuits, e.g., data provider device 102 may comprise a fairness encryption circuit and/or categorization device 103 may comprise a fairness decryption unit. The circuits implement the corresponding units described herein. The circuits may be a processor circuit and storage circuit, the processor circuit executing instructions represented electronically in the storage circuits.

Figure 8A:
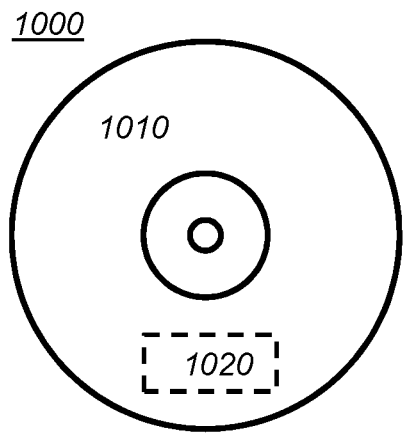
FIG. 8a schematically shows a computer readable medium having a writable part comprising a computer program according to an embodiment, FIG. 8b schematically shows an exemplary hardware diagram for implementing a device according to an embodiment.

FIG. 8a shows a computer readable medium 1000 having a writable part 1010 comprising a computer program 1020, the computer program 1020 comprising instructions for causing a processor system to perform a client method, a data provider method, and/or a categorization method, according to an embodiment. The computer program 1020 may be embodied on the computer readable medium 1000 as physical marks or by means of magnetization of the computer readable medium 1000. However, any other suitable embodiment is conceivable as well. Furthermore, it will be appreciated that, although the computer readable medium 1000 is shown here as an optical disc, the computer readable medium 1000 may be any suitable computer readable medium, such as a hard disk, solid state memory, flash memory, etc., and may be non-recordable or recordable. The computer program 1020 comprises instructions for causing a processor system to perform the client, data provider, and/or categorization method.

Figure 8B:
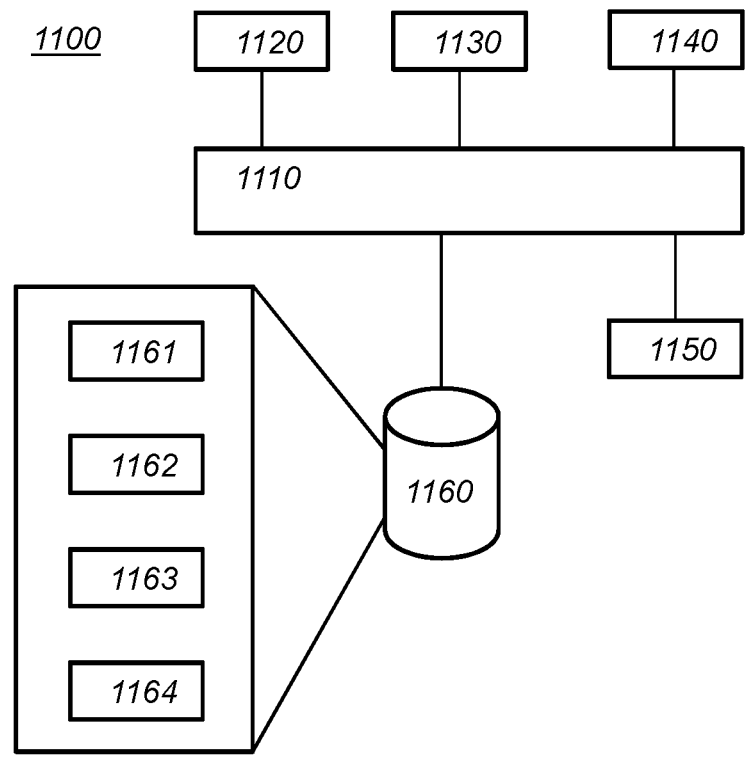

FIG. 8b illustrates an exemplary hardware diagram 1100 for implementing a client device, data provider device, and/or categorization device. The exemplary hardware 1100 may correspond to one or more of devices 101-103, 201-203, 301-303, 401-403, 501-503, or 601-603 of FIGS. 1-6. As shown, the device 1100 includes a processor 1120, memory 1130, user interface 1140, communication interface 1170, and storage 1160 interconnected via one or more system buses 1110. It will be understood that this figure constitutes, in some respects, an abstraction and that the actual organization of the components of the device 1100 may be more complex than illustrated.

The processor 1120 may be any hardware device capable of executing instructions stored in memory 1130 or storage 1160 or otherwise processing data. As such, the processor may include a microprocessor, field programmable gate array (FPGA), application-specific integrated circuit (ASIC), or other similar devices. For example, the processor may be an Intel Core i7 processor, ARM Cortex-R8, etc. In an embodiment, the processor may be ARM Cortex M0.

The memory 1130 may include various memories such as, for example L1, L2, or L3 cache or system memory. As such, the memory 1130 may include static random access memory (SRAM), dynamic RAM (DRAM), flash memory, read only memory (ROM), or other similar memory devices. It will be apparent that, in embodiments where the processor includes one or more ASICs (or other processing devices) that implement one or more of the functions described herein in hardware, the software described as corresponding to such functionality in other embodiments may be omitted. In the case of a temporary memory, the memory may contain means to obtain data before use, e.g., over an optional network connection.

The user interface 1140 may include one or more devices for enabling communication with a user such as an administrator. For example, the user interface 1140 may include a display, a mouse, and a keyboard for receiving user commands. In some embodiments, the user interface 1140 may include a command line interface or graphical user interface that may be presented to a remote terminal via the communication interface 1170.

The communication interface 1170 may include one or more devices for enabling communication with other hardware devices. For example, the communication interface 1170 may include a network interface card (NIC) configured to communicate according to the Ethernet protocol. For example, the communication interface 1170 may comprise an antenna, connectors or both, and the like. Additionally, the communication interface 1170 may implement a TCP/IP stack for communication according to the TCP/IP protocols. Generally, communication interface 1170 may be a network interface to a local or wide area network, e.g., the Internet, a storage interface to an internal or external data storage, a keyboard, an application interface (API), etc. Various alternative or additional hardware or configurations for the communication interface 1170 will be apparent.

The storage 1160 may include one or more machine-readable storage media such as read-only memory (ROM), random-access memory (RAM), magnetic disk storage media, optical storage media, flash-memory devices, or similar storage media. In various embodiments, the storage 1160 may store instructions for execution by the processor 1120 or data upon with the processor 1120 may operate. For example, the storage 1160 may store a base operating system 1161 for controlling various basic operations of the hardware 1100. The storage may also store instructions 1162-1164 to determine categorization data, determine difference encryptions, determining matches of values of a sensitive data field, etc.

It will be apparent that various information described as stored in the storage 1160 may be additionally or alternatively stored in the memory 1130. In this respect, the memory 1130 may also be considered to constitute a "storage device" and the storage 1160 may be considered a "memory." Various other arrangements will be apparent. Further, the memory 1130 and storage 1160 may both be considered to be "non-transitory machine-readable media." As used herein, the term "non-transitory" will be understood to exclude transitory signals but to include all forms of storage, including both volatile and non-volatile memories.

While device 1100 is shown as including one of each described component, the various components may be duplicated in various embodiments. For example, the processor 1120 may include multiple microprocessors that are configured to independently execute the methods described herein or are configured to perform steps or subroutines of the methods described herein such that the multiple processors cooperate to achieve the functionality described herein. Further, where the device 1100 is implemented in a cloud computing system, the various hardware components may belong to separate physical systems. For example, the processor 1120 may include a first processor in a first server and a second processor in a second server.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb 'comprise' and its conjugations does not exclude the presence of elements or steps other than those stated in a claim. The article 'a' or 'an' preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

In the claims references in parentheses refer to reference signs in drawings of exemplifying embodiments or to formulas of embodiments, thus increasing the intelligibility of the claim. These references shall not be construed as limiting the claim.

The invention claimed is:

1. A categorization system for categorizing a sensitive data field in a dataset, the dataset comprising one or more records, each record of the dataset comprising a value of the sensitive data field, the system comprising a client device, a data provider device and a categorization device, wherein:
the client device is for obtaining the categorization, said device comprising:
  a memory configured to store categories of the sensitive data field for records of the dataset;
  a processor configured to:
    determine categorization data, the categorization data comprising, for one or more possible values of the sensitive data field, a homomorphic encryption of the one or more possible values and data encoding a category of the one or more possible values;
    provide the categorization data to the data provider device;
    obtain from the categorization device data encoding a category of the sensitive data field for a record of the dataset of the one or more records, and store said category for the record in the memory;
the data provider device is for providing data to be categorized, said device comprising:
  a memory configured to store the dataset;
  a processor configured to:
    obtain the categorization data from the client device, the categorization data comprising a homomorphic encryption of a possible value of the sensitive data field of the one or more possible values and data encoding a category of the possible value;
    determine, for the record of the dataset, a homomorphic encryption indicative of a difference between said possible value and a value of the sensitive data field for the record based on the homomorphic encryption of the possible value;
    provide, to the categorization device, data encoding the category of the possible value and the homomorphic encryption indicative of the difference;
the categorization device is for enabling said categorization, said device comprising:
  a memory configured to store a decryption key for the homomorphic encryptions;
  a processor configured to:
    obtain, from the data provider device, data encoding a category of the possible value of the sensitive data field and a homomorphic encryption indicative of a difference between the possible value and a value of the sensitive data field for the record of the dataset;
    determine if the value of the sensitive data field for the record matches the possible value from said homomorphic encryption using the decryption key, and in response to determining that the value of the sensitive data field for the record matches the possible value, associate said category to the record;
    provide, to the client device, data encoding the category associated to the record.

2. A client device for obtaining a categorization of a sensitive data field in a dataset, the dataset comprising one or more records, each record of the dataset comprising a value of the sensitive data field, the client device comprising:
  a communication interface configured for digital communication with a data provider device and a categorization device;
  a memory configured to store categories of the sensitive data field for records of the dataset;
  a processor configured to:
    determine categorization data, the categorization data comprising, for one or more possible values of the sensitive data field, a homomorphic encryption of the one or more possible values and data encoding a category of a possible value of the one or more possible values;
    provide the categorization data to the data provider device;
    obtain from the categorization device data encoding a category of the sensitive data field for a record of the dataset, and store said category for the record in the memory.

3. The client device according to claim 2, wherein the dataset comprises electronic medical records and/or the sensitive data field comprises a disease classification.

4. The client device according to claim 2, wherein determining the categorization data comprises encrypting at least one possible value of the sensitive data field multiple times.

5. The client device according to claim 2, further configured to obtain values of one or more additional fields for the record, and store said values for the record in the memory.

6. A data provider device for providing data for categorizing a sensitive data field in a dataset, the dataset comprising one or more records, each record of the dataset comprising a value of the sensitive data field, the data provider device comprising:
  a communication interface configured for digital communication with a client device and a categorization device;
  a memory configured to store the dataset;
  a processor configured to:
    obtain categorization data from the client device, the categorization data comprising a homomorphic encryption of a possible value of the sensitive data field and data encoding a category of the possible value;
    determine, for a record of the dataset, a homomorphic encryption indicative of a difference between said possible value and a value of the sensitive data field for the record based on the homomorphic encryption of the possible value;
    provide, to the categorization device, data encoding the category of the possible value and the homomorphic encryption indicative of the difference.

7. The data provider device according to claim 6, further configured to, for a first homomorphic encryption and a second homomorphic encryption of the categorization data having the same category, determine a homomorphic encryption indicative of a difference between a possible value encrypted by the first homomorphic encryption and a possible value encrypted by the second homomorphic encryption, and provide said homomorphic encryption indicative of a difference to the categorization device.

8. The data provider device according to claim 6, further configured to obtain a coarse categorization of the set of possible values of the sensitive data field, wherein the categorization data is categorization data for a coarse category of the coarse categorization and the value of the sensitive data field for the record is comprised in the coarse category of the coarse categorization.

9. A categorization device for enabling a categorization of a sensitive data field in a dataset, the dataset comprising one or more records, each record of the dataset comprising a value of the sensitive data field, the categorization device comprising:
- a communication interface configured for digital communication with a client device and a data provider device;
- a memory configured to store a decryption key for homomorphic encryptions;
- a processor configured to:
  - obtain, from the data provider device, data encoding a category of a possible value of the sensitive data field and a homomorphic encryption indicative of a difference between the possible value and a value of the sensitive data field for a record of the dataset;
  - determine if the value of the sensitive data field for the record matches the possible value from said homomorphic encryption using the decryption key, and in response to determining that the value of the sensitive data field for the record matches the possible value, associate said category to the record;
  - provide, to the client device, second data encoding the category associated to the record.

10. The categorization device according to claim 9, further configured to, for a first homomorphic encryption and a second homomorphic encryption of the categorization data having the same category, obtain from the data provider device a homomorphic encryption indicative of a difference between a first possible value encrypted by the first homomorphic encryption and a second possible value encrypted by the second homomorphic encryption; and signal an error if said homomorphic encryption indicates a match of the encrypted possible values.

11. The categorization device according to claim 9, wherein the categorization device is configured to count a number of records to which a given category is associated; and to signal an error if said count is below a predefined threshold.

12. The categorization device according to claim 11 wherein the categorization device is configured to, if an error is signaled, associate a generalized category to at least each record to which said given category is associated.

13. The categorization device according to claim 9, wherein the categorization device is configured to associate a default category to the record if the value of the sensitive data field for the record does not match a third possible value according to an obtained homomorphic encryption.

* * * * *